United States Patent [19]

Baldwin et al.

[11] Patent Number: 4,769,325

[45] Date of Patent: Sep. 6, 1988

[54] 2-(ALLENYL)PENICILLINS

[76] Inventors: Jack E. Baldwin, The Dyson Perrins Laboratory, University of Oxford, South Parks Road, Oxford OX1 3QY, United Kingdom; Amit Basak, Department of Chemistry, Presidency College, 86/1 College Street, Calcutta 7000073, India

[21] Appl. No.: 891,434

[22] Filed: Jul. 28, 1986

[30] Foreign Application Priority Data

Jul. 31, 1985 [GB] United Kingdom ................ 8519264

[51] Int. Cl.$^4$ .................... C12P 37/00; C07D 499/02; C07D 499/44; C07C 149/40
[52] U.S. Cl. ...................................... 435/43; 540/312; 540/314; 540/329; 540/331; 540/335; 560/16; 560/17; 560/147; 560/148; 560/153; 562/430; 562/431; 562/555; 562/556; 558/37
[58] Field of Search ............... 540/314, 329, 331, 335, 540/312; 562/555, 556, 430, 431; 560/148, 149, 16, 17, 153; 435/48; 558/37

[56] References Cited

U.S. PATENT DOCUMENTS 4,215,118  7/1980  Priess et al. .................... 540/328 X

OTHER PUBLICATIONS

Bahadur, et al., *J.C.S. Chem. Comm.*, pp. 917–919, Dec., (1981).
Baldwin, et al., *J.C.S. Chem. Comm.*, pp. 1211–1214, Dec., (1984).

Primary Examiner—Werren B. Lone
Assistant Examiner—Vera C. Clarke
Attorney, Agent, or Firm—William B. Scanlon; Leroy Whitaker

[57] ABSTRACT 2-(Allenyl)penicillins antibiotics and intermediates thereto are disclosed. A process for making the 2-(allenyl)penicillins and the starting materials for the process are also disclosed.

16 Claims, No Drawings

2-(ALLENYL)PENICILLINS

BACKGROUND OF THE INVENTION

This invention relates to new penicillin compounds and to processes for their production.

Penicillins are widely used for the treatment of diseases caused by pathogenic bacteria in human beings and animals. Although the effectiveness of these antibiotics is acknowledged, it is recognized that there is a need for new, improved, active compounds, for example to avoid the problems of allergy or the development of resistance in bacteria associated with the use of existing penicillins.

A significant amount of research has been directed to obtain such compounds, and a large number of penicillins have been prepared, usually by molecular modification of existing compounds. Not all molecular modifications have been successful. Thus attention has tended to focus on variation of the 6β-side chain since in general it has been found that alteration to the β-lactam or thiazolidine rings and/or the other substituents they carry may lead to diminution and sometimes elimination of antibiotic activity.

We have now found that the thiazolidine ring in penicillins may be substituted with an allenyl group to produce a novel class of compounds which have antibiotic activity and/or are of interest as intermediates for the production of penicillins with antibiotic activity.

SUMMARY OF THE INVENTION

One aspect of this invention is directed to penicillin antibiotics (and the immediate precursors therefor) of the formulas

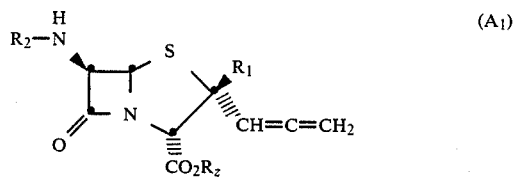

(A₁)

or

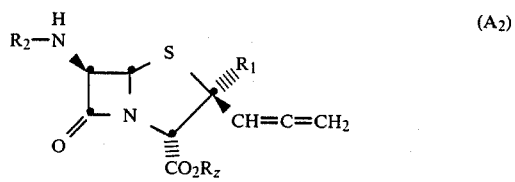

(A₂)

or a mixture of the two. R₁, R₂, and R$_z$ in the above formulas are as defined below.

Another aspect of the invention encompasses intermediates to the above penicillins of the formula

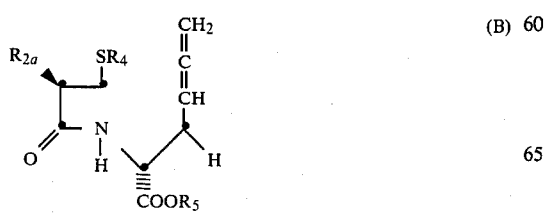

(B)

and the corresponding disulphide intermediates of the formula

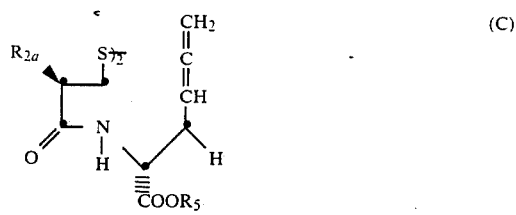

(C)

wherein R$_{2a}$, R₄, and R₅ are as defined below.

A further aspect of the invention is a process for making the compounds of Formula A₁ and A₂ above, wherein in the Formulas R₂ is a group of the formula

wherein R₆ is a group of the formula

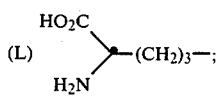

(L)

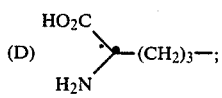

(D)

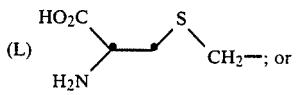

(L)

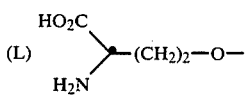

(L)

and also wherein R$_z$ and R₅ are hydrogen;
which comprises combining a substrate compound of the formula

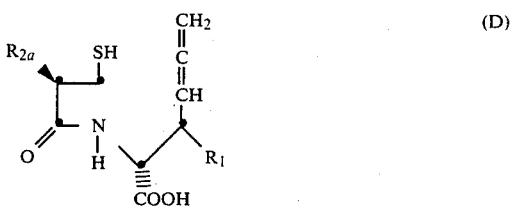

(D)

or a substrate compound of the formula

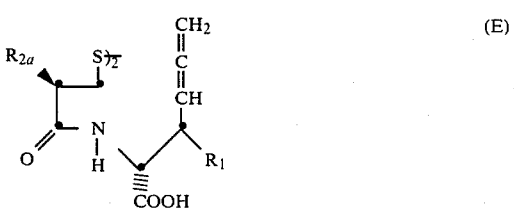

(E)

with the enzyme known as isopenicillin N synthetase. In the above Formulas (D) and (E), $R_1$ and $R_{2a}$ are as defined below.

DETAILED DESCRIPTION

Thus according to one aspect of the invention we provide compounds of the general Formula (1a) and (1b):

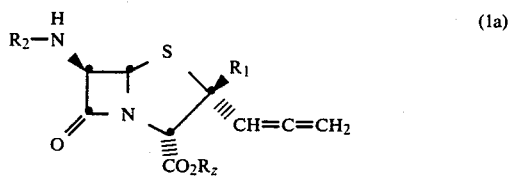
(1a)

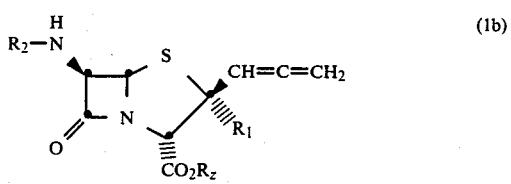
(1b)

wherein $R_1$ represents hydrogen or a methyl group, $R_2$ represents hydrogen, an amino-protecting group or a $C_1$ to $C_{20}$ acyl group; and $R_z$ is a carboxy-protecting group or hydrogen; or a salt thereof.

When $R^2$ represents an amino-protecting group it may be, for example, a $C_1$ to $C_{20}$ acyl group used for protecting amino groups such as a group $R_3$ in which $R_3$ represents a $C_7$ to $C_{20}$ aralkyl (e.g. benzyl), a $C_7$ to $C_{20}$ aryloxyalkyl (e.g. phenoxymethyl) or an optionally substituted $C_1$ to $C_6$ alkyl, $C_1$ to $C_6$ alkoxy, or $C_1$ to $C_6$ group.

Substituents that may be present on the group $R_2$ include for example carboxyl and amino groups.

The term "$C_i$ to $C_{20}$ acyl group" represented by $R_2$ refers to the acyl moieties (other than those traditionally used as amino-protecting groups) which have been bonded to the C-6 amino group of penicillins, the C-7 amino group of cephalosporins, 1-oxadethiacephalosporins or 1-carbacephalosporins, and the C-3 amino of monocyclic β-lactams (such as the azthreonam series). The "$C_1$ to $C_{20}$ acyl group" can be optionally interrupted by heteroatoms. Examples of such acyl groups can be found in references such as "Cephalosporins and Penicillins, Chemistry and Biology" edited by Edwin W. Flynn, Academic Press, New York, 1972 and "Chemistry and Biology of β-Lactam Antibiotics" edited by Robert B. Morin and Marvin Gorman, Vols. 1, 2, and 3, Academic Press, New York, 1982.

Examples of $C_1$ to $C_{20}$ acyl groups at $R_2$ can also be found in U.S. Pat. Nos. 4,478,997, M. Yoshioka et al., issued Oct. 23, 1984, 4,172,199, B. R. Belleau et al., issued Oct. 23, 1979, 4,472,300, T. Kamiya et al., issued Sept. 18, 1984, (especially columns 25 through 36) all of which are herein incorporated by reference. Additional examples of "acyl groups derived from a $C_1$ to $C_{20}$ carboxylic acid" can be found in Koster et al., U.S. Pat. No. 4,478,749, issued Oct. 23, 1984.

Some specific examples of the $C_1$ to $C_{20}$ acyl groups of $R_2$ include groups wherein $R_2$ is a group of the formula

wherein $R_6$ is
(i) 1,4-cyclohexadienyl, 1-cyclohexenyl, phenyl or substituted phenyl, wherein the substituents are 1 or 2 halogen, hydroxy, protected hydroxy, amino, protected amino, nitro, cyano, trifluoromethyl, $C_1$ to $C_4$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or N-(($C_1$ to $C_4$ alkyl)sulfonylamino) groups;
(ii) a group of the formula

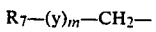

wherein y is O or S, m is 0 or 1, $R_7$ is $R_6$ as defined above, and when m is 0, $R_7$ is also 2-thienyl, 3-thienyl, 2-furyl, 3-furyl, 1-tetrazolyl, 5-tetrazolyl, 2-thiazolyl, 2-aminothiazol-4-yl, or 2-(protected amino)thiazol-4-yl;
(iii) a group of the formula

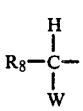

wherein
$R_8$ is $R_7$ as defined above, a 2- or 3-indolyl group, a substituted 2- or 3-indolyl group of the formula

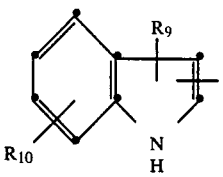

in which $R_9$ and $R_{10}$ independently are hydrogen, halo, hydroxy, protected hydroxy, $C_1$ to $C_4$ alkyl, $C_1$ to $C_4$ alkoxy, nitro, amino, protected amino, N-(($C_1$ to $C_4$ alkanoyl)amino), N-(($C_1$ to $C_4$ alkyl)sulfonylamino), or when $R_9$ and $R_{10}$ are on adjacent carbon atoms, they may be taken together to form a methylenedioxy group; a 2- or 3-benzothienyl group, a 2- or 3-substituted benzothienyl group of the formula

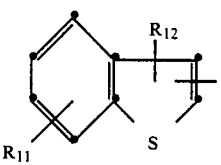

in which $R_{11}$ and $R_{12}$ are independently hydrogen, halo, hydroxy, protected hydroxy, $C_1$ to $C_4$ alkyl, $C_1$ to $C_4$ alkoxy, nitro, amino, protected amino, N-(($C_1$ to $C_4$ alkanoyl)amino), N-(($C_1$ to $C_4$ alkyl)sulfonylamino), or when $R_{11}$ and $R_{12}$ are on adjacent carbon atoms, they can be taken together to form a methylenedioxy group;

a 1- or 2-naphthyl group, a substituted 1- or 2-naphthyl group of the formula

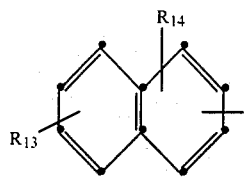

wherein $R_{13}$ and $R_{14}$ are independently hydrogen, halo, hydroxy, protected hydroxy, $C_1$ to $C_4$ alkyl, $C_1$ to $C_4$ alkoxy, nitro, amino, protected amino, N-(($C_1$ to $C_4$ alkanoyl)amino), N-(($C_1$ to $C_4$ alkyl)sulfonylamino), or when $R_{13}$ and $R_{14}$ are on adjacent carbon atoms, they can be taken together to form a methylenedioxy group; and W is amino, protected amino, carboxy, protected carboxy, or sulfonato;

(iv) a group of the formula

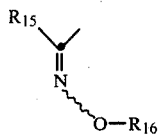

wherein $R_{15}$ is phenyl, p-(O-(homoserine))phenyl, thien-2-yl, fur-2-yl, 2-aminothiazol-4-yl, 2-(protected amino)thiazol-4-yl, 5-amino-1,2,4-thiadiazol-3-yl, 5-(protected amino)-1,2,4-thiadiazol-3-yl, 4-aminopyridin-2-yl, 4-(protected amino)pyridin-2-yl, 2-aminopyridin-6-yl, 2-(protected amino)pyridin-6-yl, 2-aminopyrimidin-4-yl, 2-(protected amino)pyrimidin-4-yl, 4-aminopyrimidin-2-yl, or 4-(protected amino)-pyrimidin-2-yl; and $R_{16}$ is hydrogen, methyl, ethyl, propyl, 2-carboxyisopropyl, 2-(protected carboxy)isopropyl, carboxymethyl, (protected carboxy)methyl, cyclopropyl, cyclobutyl, cyclopentyl, benzyl, phenyl, 4-fluorophenyl, 4-chlorophenyl, 3-(trifluoromethyl)phenyl, 3-(ethoxycarbonyl)phenyl, 2-methylphenyl, 4-methylphenyl, 3,4-dichlorophenyl, or 2,4-dichlorophenyl; or (v) a group of the formula

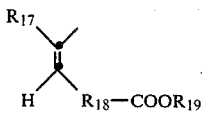

wherein $R_{17}$ is phenyl, furyl, thienyl, oxazolyl, isoxazolyl, aminoisoxazolyl, (protected amino)isoxazolyl, thiazolyl, aminothiazolyl, or (protected amino)thiazolyl;

$R_{18}$ is $C_1$ to $C_3$ alkyl; and $R_{19}$ is hydrogen or a carboxy-protecting group;

(vi) a group of the formula

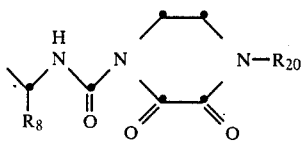

wherein $R_8$ is as defined above and $R_{20}$ is $C_1$ to $C_6$ alkyl or $C_1$ to $C_6$ substituted alkyl;

(vii) a group of the formula

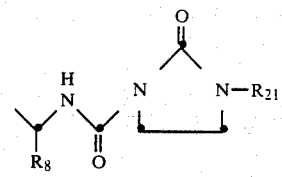

wherein $R_8$ is as defined above and $R_{21}$ is hydrogen, $C_1$ to $C_4$ alkylsulfonyl, a group of the formula

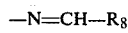

(wherein $R_8$ is as defined above); a group of the formula

wherein $R_{22}$ is hydrogen, $R_8$, $C_1$ to $C_6$ alkyl or $C_1$ to $C_6$ substituted alkyl; or (viii) a group of the formula

$HO_2C(CH_2)_3-$;

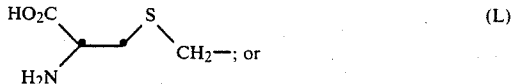

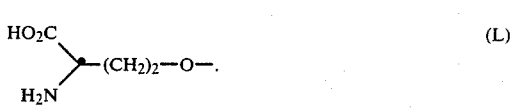

As used in conjunction with the above examples of specific acyl groups, the terms "halogen" or "halo" denotes a fluoro, chloro, bromo or iodo atom. The term "$C_1$ to $C_3$ alkyl" indicates a methyl, ethyl, n-propyl, or iso-propyl group. The term "$C_1$ to $C_4$ alkyl" embraces the groups indicated by the term "$C_1$ to $C_3$ alkyl" plus the n-butyl, iso-butyl, sec-butyl and tert-butyl groups.

The term "$C_1$ to $C_6$ alkyl" denotes such radicals as methyl, ethyl, n-propyl, iso-propyl, n-butyl, sec-butyl, tert-butyl, amyl, tert-amyl, hexyl and the like. The preferred "$C_1$ to $C_6$ alkyl" group is methyl.

The term "$C_1$ to $C_6$ substituted alkyl" denotes the above $C_1$ to $C_6$ alkyl groups that are substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl and the like. A preferred group of examples within the above "$C_1$ to $C_6$ substituted alkyl" group includes the substituted methyl group, in other words, a methyl group substituted by the same substituents as the "$C_1$ to $C_6$ substituted alkyl" group. Examples of the substituted methyl group include groups such as hydroxymethyl, protected hydroxymethyl, (e.g., tetrahydropyranyloxymethyl), acetoxymethyl, carbamoyloxymethyl, chloromethyl, bromomethyl and iodomethyl.

The term "$C_1$ to $C_4$ alkoxy" as used herein denotes groups such as methoxy, ethoxy, n-propoxy, iso-propoxy, n-butoxy, t-butoxy and like groups. The term "$C_1$ to $C_7$ acyloxy" denotes herein groups such as formyloxy, acetoxy, propionyloxy, butyryloxy, pentanoyloxy, hexanoyloxy, heptanoyloxy, and the like. The term "$C_1$ to $C_7$ alkylsulfonyl" indicates groups such as methylsulfonyl, ethylsulfonyl, n-propylsulfonyl, iso-butylsulfonyl, and the like. The term "N-(($C_1$ to $C_4$ alkanoyl)amino)" includes groups such as formylamino, acetylamino, n-propionylamino and iso-butyrylamino moieties. Examples of the term "N-(($C_1$ to $C_4$ alkyl)sulfonylamino)" include the N-(methylsulfonylamino), N-(ethylsulfonylamino), N-((iso-propyl)sulfonylamino), and the N-((n-butyl)sulfonylamino) groups.

The term "hydroxy-protecting group" refers to a readily cleavable group bonded to a hydroxyl group, such as the formyl, chloroacetyl, tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, p-nitrobenzyl, allyl, trimethylsilyl, (t-butyl)dimethylsilyl, and the 2,2,2-trichloroethoxycarbonyl groups. Further examples of hydroxy-protecting groups are described by C. B. Reese and E. Haslam, "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. Some preferred hydroxy-protecting groups are the trityl group and the tetrahydropyranyl group. Also, hydroxyl groups substituted by such hydroxy-protecting groups are referred to herein as "protected hydroxy" groups.

As used in conjunction with the above examples of acyl groups, examples of the term "$C_1$ to $C_4$ alkanoyl" include groups such as the formyl, acetyl, n-propionyl, iso-propionyl, n-butyryl, and iso-butyryl groups.

Examples of the term "substituted phenyl" as used herein include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 4-iodophenyl, 2-fluorophenyl, and the like; a mono- or di(hydroxy)phenyl group such as 4-hydroxyphenyl, 3-hydroxyphenyl, 2,4-dihydroxyphenyl, the protected-hydroxy derivatives thereof, and the like; a nitrophenyl group such as the 3- or 4-nitrophenyl group; a cyanophenyl group, for example, 4-cyanophenyl; a mono- or di(amino)phenyl group such as 4-aminophenyl, 3,5-di(amino)phenyl, 2-aminophenyl, the (protected-amino)phenyl analogs thereof, and the like; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl, and the like; a mono- or di(alkoxy)phenyl group, for example, 2,6-dimethoxyphenyl, 4-methoxyphenyl, 3-ethoxyphenyl, 4-(iso-propoxy)phenyl, 4-(t-butoxy)phenyl, 3-ethoxy-4-methoxyphenyl, and the like; 3- or 4-(trifluoromethyl)phenyl; a mono- or dicarboxyphenyl or (protected carboxy)phenyl group such as 4-carboxyphenyl or 2,4-di(protected carboxy)phenyl, a mono- or di(hydroxymethyl)phenyl or (protected hydroxymethyl)phenyl group such as 3-(protected hydroxymethyl)phenyl or 3,4-di(hydroxymethyl)phenyl; a mono- or di(aminomethyl)phenyl or (protected aminomethyl)phenyl group such as 2-(aminomethyl)phenyl or 2,4-di(protected aminomethyl)phenyl, or a mono- or di[N-($C_1$ to $C_4$ alkyl)sulfonylamino]phenyl group such as 3-(N-(methylsulfonylamino))phenyl, 3-(N-(ethylsulfonylamino))phenyl or 4-(N-(n-butylsulfonylamino))phenyl. Also, the term "substituted phenyl" represents disubstituted phenyl groups wherein the susbtituents are different, for example, 3-methyl-4-hydroxyphenyl, 3-chloro-4-aminophenyl, 2-methoxy-4-bromophenyl, 4-ethyl-2-aminophenyl, 3-hydroxy-4-nitrophenyl, 2-hydroxy-4-carboxyphenyl, and the like. Preferred substituted phenyl groups include the 2- and 3-(trifluoromethyl)phenyl, the 4-hydroxyphenyl, the 2-(aminomethyl)phenyl, the 3-(N-(methylsulfonylamino))phenyl, and 3-(N-(ethylsulfonylamino))phenyl groups.

In the description of the invention below, reference to compounds of Formula (1) is intended to mean compounds of general Formula (1a) and (1b) except where otherwise indicated.

The compounds of Formula (1) may form salts with bases, for example inorganic base salts such as alkali metal salts (e.g. sodium and potassium salts) and alkaline earth metal salts (e.g. calcium salts); amino acid salts (e.g. lysine and arginine salts); and organic base salts (e.g. procaine, phenylethylbenzylamine, dibenzylethylenediamine, ethanolamine, diethanolamine and N-methylglucosamine salts). When $R_2$ in the compounds of Formula (1) is, or contains, an amino group, the compounds may also form salts with acids. Such salts include acid addition salts, e.g. formed with hydrochloric, hydrobromic, sulphuric, nitric, phosphoric, formic and trifluoroacetic acids. For therapeutic applications, salts of compounds of Formula (1) will desirably be physiologically acceptable salts.

Compounds according to the invention have been found to exhibit antibiotic activity, in particular against strains of *Staphylococcus aureus*. The compounds may be of use in the treatment of a variety of diseases caused by pathogenic bacteria in human beings and animals, such as respiratory tract infections and urinary tract infections.

The compounds of the invention are also useful as intermediates for the production of penicillins with antibiotic activity.

For use in human or veterinary medicine, the compounds of the invention may be formulated in any convenient way, by analogy with other antibiotics. The invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form, in ampoules, or in multidose containers, if necessary with an added preservative. The compositions may also take such forms as suspensions, solutions, or emulsions in oily or aqueous vehicles, and may contain formulatory agents such as suspending, stabilizing and/or dispersing agents. Alternatively the active ingredient may be in powder form for reconstitution with a suitable vehicle, e.g. sterile pyrogen-free water, before use.

The compositions may also be presented in a form suitable for absorption by the gastro-intestinal tract, for example, tablets, capsules, syrups or suspensions for oral administration, and suppositories.

Compositions for veterinary medicine may, for example, be formulated as intramammary preparations in either long acting or quick-release bases.

The compositions may contain from 0.1% upwards, e.g. 0.1-99% of the active material, depending on the method of administration. When the compositions comprise dosage units, each unit will preferably contain 50 to 2000 mg of the active ingredient, e.g. 250 to 500 mg. The daily dosage for adult human treatment will preferably range from 250 to 5000 mg e.g. 500 to 2000 mg per day, depending inter alia on the nature of the infection and the route and frequency of administration. In genera, intravenous or intramuscular administration will be employed, for example using 500 to 2500 mg per day of the active ingredient in adult human treatment.

The antibiotic compounds according to the invention may be administered in combination with other therapeutic agents such as antibiotics, for example other penicillins or cephalosporins.

The compounds according to the invention may be prepared by a number of processes, as described in the following wherein $R_1$ is as defined for general Formula (1).

In particular, we have found that it is possible to prepare certain compounds of Formula (1) using an enzyme-catalysed cyclization process. This process is new and forms a further feature of the invention.

Thus, according to another embodiment of the invention we provide a process for the conversion of compounds of Formula (2)

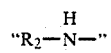

(wherein $R_{2a}$ represents

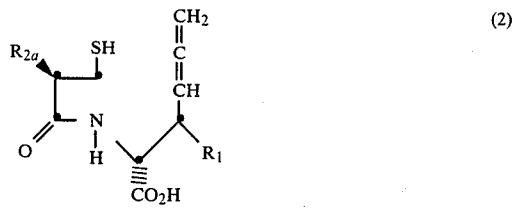

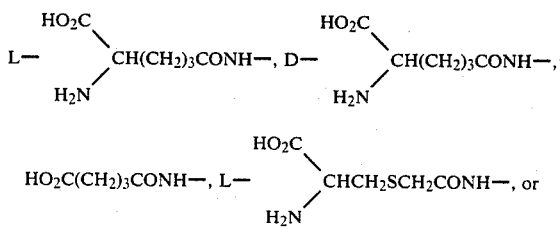

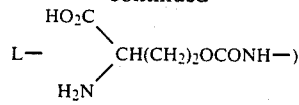

and the corresponding disulphides and salts thereof to a compound of Formula (1) [in which the group "$R_2-\overset{H}{N}-$"

is as defined for $R_{2a}$ in Formula (2)] by cyclization catalyzed by an isopenicillin N synthetase enzyme.

Where an individual isomer of Formula (1a) or (1b) is desired, this may be obtained by conventional means, e.g. by chromatography or electrophoresis of a mixture of isomers of Formula (1a) and (1b).

Intermediates of Formula (2) in which $R_1$ is hydrogen, and the disulphides and salts thereof, are novel compounds and form a further aspect of the invention.

Suitable salts of the compounds of Formula (2) include salts with inorganic or organic bases e.g. alkali metal, alkaline earth metal and amine salts and, when $R_{2a}$ contains an amino group, salts with acids, e.g. acid addition salts.

The isopenicillin N synthetase may be derived from a microorganism which produces the enzyme, such as a species of the genus Acremonium, Streptomyces or Penicillium. Particularly suitable species which may be employed to provide the desired isopenicillin N synthetase activity include *Acremonium chrysoqenum*, for example strains IMI 237183, ATCC 20339, ATCC 14553, ATCC 36255, ATCC 48272, and NRRL 11418; *Streptomyces cattleya*, for example strain NRRL 8057, *Streptomyces lipmanii*, for example strain NRRL 3584 and *Streptomyces clavuligerus*, for example strains ATCC 27064 and NRRL 3585; and *Penicillium chrysogenum*, for example strain NRRL 1951. Selectants or mutants of the strains mentioned above may also be employed.

A particularly preferred strain is *Acremonium chrysogenum* IMI 237183 or a selectant or mutant thereof.

As used herein, the term 'selectant' means a strain of the microorganism derived from colony selected from the parent strain which has been cultivated in such a way as to provide a strain having one or more properties which are qualitatively or quantitatively different from those of the parent strain e.g. resistance to substances produced in fermentation. Such a selectant may, of course, be a spontaneous mutant of the parent microorganism, but in some it may not be.

As used herein, the term 'mutant' will include any mutant strain which arises either spontaneously or as a result of the action of an external agent, which may be either deliberately applied or otherwise. Mutant strains may be produced by a variety of methods including the use of ionizing radiation (e.g., u.v. light, X- and γ-rays) chemicals (e.g., nitrous oxide, hydroxylamine, pyrimidine base analogues such as 5-bromouracil, acridines, alkylating agents such as mustard gas, hydrogen peroxide, phenols, and formaldehyde) heat and genetic techniques (e.g. recombination, transduction, transformation, lysogenisation, lysogenic conversion, and selective techniques for spontaneous mutants).

In the process catalysed by the isopenicillin N synthetase, the substrate of Formula (2) may be incubated with a preparation of the enzyme, optionally in buffer solution, at, for example 0°–40° C., preferably 20° to 30° C., at a pH preferably in the range 6 to 9, e.g., in the range 7.0 to 8.0. It is advantageous to supply one or more cofactors selected from reducing agents e.g. dithiothreitol, for example at a concentration of from 1 to 5 mM, ferrous ions (e.g. provided by ferrous sulphate) at a concentration of from 0.1 to 1 mM and ascorbate ions (e.g. provided by ascorbic acid) at a concentration of from 1 to 5 mM, and oxygen. If desired catalase may be added to the reaction mixture, for example 1000–5000 (e.g. 3000) Sigma units/ml.

The reaction may be quenched by, for example, the addition of solvents such as acetone, and any precipitated protein removed e.g. by centrifugation. The desired compound of the invention may then be recovered using conventional techniques such as solvent extraction.

The isopenicillin N synthetase preparation used in the process may be obtained from the fermentation of a microorganism which produces the enzyme. The fermentation may be performed using methods well known in the art for example those described by Fawcett et al (1975) *Biochem. J.* 151, 741–746, Fawcett et al. (1976) *Biochem. J.* 157, 651–660, and O'Sullivan et al. (1979) *Biochem. J.* 179, 47–52.

The synthetase preparation used in the process will generally be a cell-free extract obtained from the fermentation using conventional methods for the isolation and purification of enzymes. Where the enzyme is cell-bound it may be released for use by conventional techniques such as grinding with glass beads, homogenisation or sonication after suspension of the cells in a suitable buffer. The crude enzyme preparation may if desired be purified further using well-known methods such as fractional precipitation techniques, using for example a salt such as protamine sulphate or ammonium sulphate, and batch or column chromatography with ion-exchange celluloses, affinity adsorbents or molecular sieves.

If desired the enzyme may be employed in an immobilized form, e.g., by insolubilization or entrapment thereof on, or in, a suitable matrix. Thus an extract of the enzyme may be covalently bound or linked to an otherwise inert inorganic or organic polymer, entrapped on or in, a fibre, or on, or in, a membrane or polymer such as polyacrylamide gel, absorbed on an ion-exchange resin, cross-linked with a reagent such as gluteraldehyde, or occluded in an envelope such as a bead. Immobilised synthetases of these types may advantageously be employed both in batch processes, after which the enzyme may be reused, and continuous flow processes wherein substrates pass through a column containing the immobilized enzyme.

Intermediates of Formula (2) may be prepared by deprotection of a compound of Formula (3)

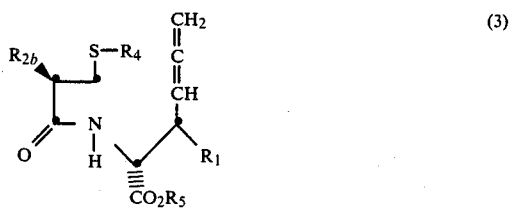

(3)

(wherein $R_{2b}$ is as defined for $R_{2a}$ in Formula (2) except that amino, hydroxy and carboxyl groups where present are protected (e.g., as p-methoxybenzyloxycarbonylamino and p-methoxybenzyloxycarbonyl groups), $R_4$ is a p-methoxybenzyl group, and $R_5$ is a diphenylmethyl group) using for example trifluoroacetic acid in the presence of anisole at an elevated temperature e.g., the reflux temperature.

Selected compounds from the above Formulas (2) and (3) are further aspects of the instant invention. In particular, compounds of Formulas (2) and (3) wherein:

$R_1$ is hydrogen;

$R_{2a}$ is a group of the formula:

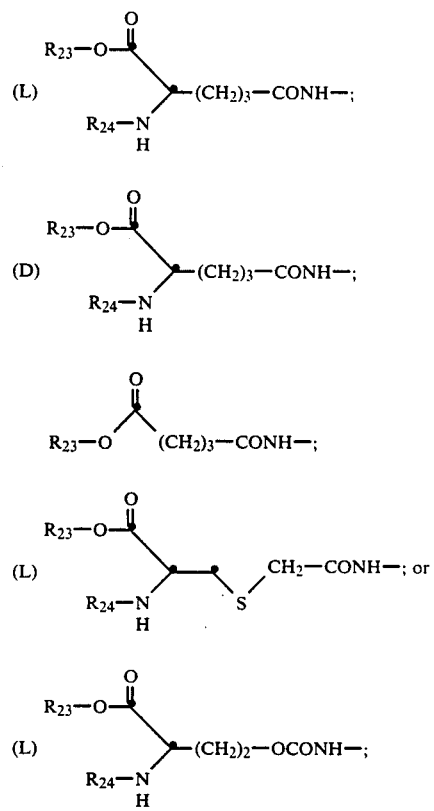

$R_4$ is hydrogen or p-methyoxybenzyl;

$R_5$ is hydrogen or a carboxy-protecting group;

$R_{23}$ is hydrogen or a carboxy-protecting group; and $R_{24}$ is hydrogen or an amino-protecting group or a salt thereof; are further embodiments of this invention.

A further aspect of the instant invention is a compound of the formula

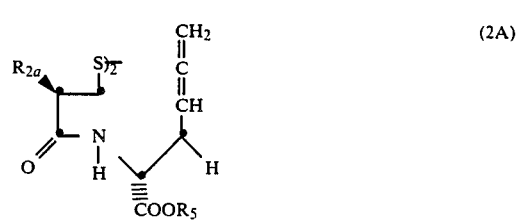

(2A)

wherein: $R_5$ is hydrogen or a carboxy-protecting group and $R_{2a}$ is a group of the formula

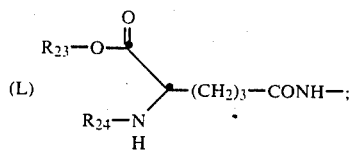
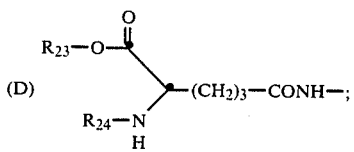
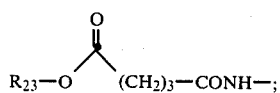
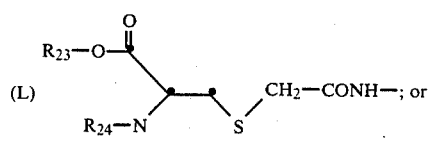
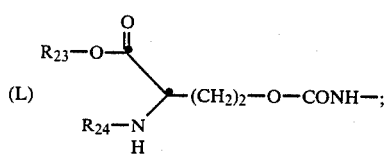

wherein $R_{23}$ is a hydrogen or a carboxy-protecting group;

$R_{24}$ hydrogen or an amino-protecting group; or a salt thereof.

Intermediates of Formula (3) may be prepared by reaction of a compound of Formula (4)

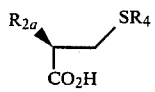

with a compound of Formula (5)

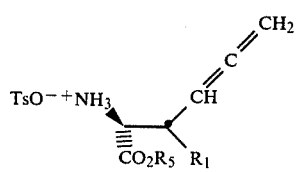

(wherein "Ts" represents p-toluenesulphonyl) in the presence of a coupling agent such as 1-ethoxycarbonyl-2-ethoxy-1,2-dihydroquinoline and a base e.g., triethylamine in a suitable solvent e.g., dichloromethane.

Intermediates of Formula (4) are either known compounds or may be prepared by methods analogous to those used for the preparation of the known compounds (see for example Baldwin et al. *J. Chem. Soc. Perkin*, 1981, 2253, and Hanessian and Sahoo, *Tet. Letters*, 1984, 25, 1425).

The intermediates of Formula (5) may be prepared from the compounds of Formula (6).

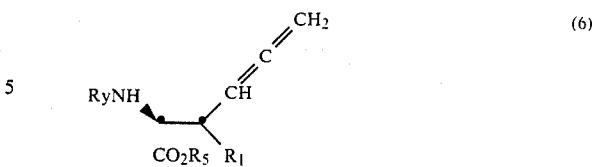

(where Ry is t-butyloxycarbonyl) by reaction with p-toluenesulphonic acid in a solvent such as ether.

The compounds of Formula (6) may be prepared from an iodoalanine of Formula (7)

by reaction with triphenyl propargyl tin and azobisisobutyronitrile in benzene.

The disulphides (Formula 2A) of the intermediates of Formula (2) may be prepared by oxidation of the corresponding sulphide using for example oxygen.

In a further process for the preparation of compounds of Formula (1), a compound of Formula (1) in which $R_2$ is hydrogen may be prepared from a corresponding compound of Formula (1) in which $R_2$ is an acylamino group by deacylation. The reaction may be effected using a nitrosyl halide such as nitrosyl chloride, at a temperature of from $-30°$ to $+20°$ C. conveniently in a solvent such as acetonitrile.

According to another process, a compound of Formula (1) where $R_2$ is an acylamino group may be prepared by acylation of a corresponding compound in which $R_2$ is hydrogen. Acylation may be effected using an acid or an activated derivative or ester thereof. Suitable activated derivatives include acid halides particularly acid chlorides or bromides and acid anhydrides.

Acylations employing acid halides may be effected in aqueous or non-aqueous reaction media, conveniently at temperatures of from $-50°$ to $+50°$ C., preferably $-40°$ to $+30°$ C. if desired in the presence of an acid binding agent such as a tertiary amine (e.g., triethylamine) an inorganic base (e.g., sodium bicarbonate) or an oxirane (e.g., ethylene oxide or propylene oxide). Suitable reaction media include aqueous ketones e.g., acetone, aqueous alcohols e.g., ethanol, esters e.g., ethyl acetate, halogenated hydrocarbons e.g., methylene chloride, amides such as dimethylacetamide nitriles such as acetonitrile, or mixtures of two or more such solvents.

Acylations employing acids are desirably conducted in the presence of a condensing agent for example a carbodiimide such as N,N$^1$-dicyclohexylcarbodiimide; a carbonyl compound such as carbonyldiimidazole; or an isoxazolium salt such as N-ethyl-5-phenylisoxazolium perchlorate.

Suitable anhydrides include symmetrical anhydrides or mixed anhydrides (e.g. formed with pivalic acid or with a haloformate such as a lower alkylhaloformate). Mixed anhydrides may also be formed with phosphorus acids (for example phosphoric or phosphorous acids), sulphuric acid or an aliphatic sulphonic acid.

Esters may conveniently be formed in situ using, for example, 1-hydroxybenzotriazole in the presence of a condensing agent as set out above. Alternatively, the ester may be preformed.

Acylation reactions involving the free acids or anhydrides or esters thereof as described above are desirably effected in an anhydrous reaction medium, e.g. methylene chloride, tetrahydrofuran, dimethylformamide or acetonitrile.

If desired, the above acylation reactions may be carried out in the presence of a catalyst such as 4-dimethylaminopyridine.

It will be appreciated that in some of the processes described above it may be necessary to protect any sensitive groups (e.g. amino, or carboxyl qroups) in the molecule of the compound in question to avoid undesirable side reactions. Conventional protection methods may be used, for example as described in "Protective Groups In Organic Chemistry" Ed. J.F.N. McOmie (Plenum Press, 1973). Examples of suitable amino protecting groups are aralkyl groups such as triphenylmethyl and acyl groups such as chloroacetyl. Suitable carboxyl protecting groups include aralkyl groups e.g. benzyl. The protecting group may thereafter be removed in any convenient way which does not cause breakdown of the desired compound e.g. triphenylmethyl and benzyl groups may be removed by hydrolysis under acidic or basic conditions as appropriate, and chloroacetyl groups may be removed by treatment with thiourea.

The following Examples illustrate the invention. All temperatures are in °C. HPLC refers to high performance liquid chromatography.

Preparation 1

Preparation of isopenicillin N synthetase

*Acremonium chrysogenum* IMI 237183 was grown as described by Fawcett et al, *Biochem. J.*, 1976, 157, 651–660, except that distilled water was used instead of tap water.

Mycelia (96 hours old/about 10 hours from the beginning of stationary phase) were harvested by filtration through a double-layer of cheese cloth, (this, and all subsequent steps described below were carried out at 2–4°), resuspended in distilled water (3 x v/w) and suction-dried through Whatman filter paper (No. 52). The resulting mycelia were suspended in 50 mM Tris-HCl buffer, pH 8.0, (3 x v/w) and disrupted in a Dyno Mill (Willy A Bacofen AG Maschinenfabrik, Basel) with 0.25 mm glass beads (500 ml stirred at 3000 r.p.m. in a 600 ml head).

A one fifth volume of protamine sulphate solution (6% w/v in distilled water) was added to the homogenate and the resulting solution stirred for 20 minutes then centrifuged at 10,000 g for 30 minutes. The supernatant was collected and ammonium sulphate was added to 55% saturation. The solution was centrifuged (10,000 g for 30 min) the supernatant was collected and ammonium sulphate was added to 85% saturation. The resulting precipitate was recovered (centrifugation at 10,000 g for 45 minutes) and dissolved in a minimum amount of Tris-HCl buffer (50 mM, pH 7.5, containing 0.015% w/v sodium azide), to obtain a protein concentration of about 40 mg/ml.

The protein solution (80 ml) was loaded onto a coarse Sephadex G-75 (Pharmacia) column (3.7 cm×110 cm) which had been pre-equilibrated with the same Tris-HCl buffer and the fractions with isopenicillin N synthetase activity were collected, pooled and loaded directly onto a DEAE-Sepharose CL-6B column (5 cm×11.5 cm) which had been pre-equilibrated with Tris-HCl buffer (50 mM, pH 7.5, containing 0.015% w/v sodium azide). The column was washed with about 500 ml of 50 mM, NaCl in the same Tris-HCl buffer then subjected to a gradient elution of NaCl in buffer (50 mM→250 mM, total volume 800 ml, linear gradient), enzyme activity being eluted at about 100 mM NaCl. The enzyme solution obtained from the column was suitable for direct-use.

Preparation 2

(a) Intermediate 1

(R)-Diphenylmethyl-2-[[(1,1-dimethylethoxy)carbonyl]amino-]-4,5-hexadienoic acid N-[(1,1-Dimethylethoxy)carbonyl]-3-iodo-D-alanine diphenylmethyl ester (48lmg), triphenyl propargyl tin (780 mg) and azobisisobutyronitrile (AIBN) (0.15 eq) were dissolved in dry degassed benzene (2 ml) and the solution was refluxed under nitrogen at 80° for 18 h. Fresh quantities of tin reagent (1 eq) and AIBN (10 mg) were added after 4, 8 and 12 h. The reaction mixture was cooled, evaporated to dryness, and the residue taken up in acetonitrile, washed with hexane then evaporated to leave an oily residue which was chromatographed over flash silica gel; dichloromethane eluates gave the title compound (247 mg) crystallized from petroleum ether-dichloromethane m.p. 53°.

(b) Intermediate 2

(R)-2-[(Diphenylmethoxy)carbonyl]-4,5-hexadien-1-aminium 4-methylbenzensulphonate A solution of anhydrous p-toluenesulphonic acid (15 mg) in ethanol was added slowly (15 min) to an ether solution of Intermediate 1 (34 mg) at $-5°$ to $-10°$. The solution was stirred at room temperature under argon for 3 h then evaporated to dryness to leave the title compound (40 mg) m.p. 128°–130°.

(c) Intermediate 3

[2R-[2(R*),2(S*),2(S*)]]-Diphenylmethyl-2-[[2-[[6-[(4-methoxyphenyl)methoxy]carbonyl]amino]-1,6-dioxohexyl]-amino]-3-[[(4-methoxyphenyl)methyl]thio-1-oxopropyl]amino]-4,5-hexadienoate To a solution of 5-[[[(4-methoxyphenyl)methoxy]carbonyl]amino]-5-[[[(4-methoxyphenyl)methoxy]carbonyl]-1-oxopentyl]-L-2-amino-3-[[(4-methoxyphenyl)methyl]thio]propanoic acid (66 mg) in dry dichloromethane (4 ml) was added Intermediate 2 (40 mg), triethylamine (12 µl), and 1-ethoxycarbonyl-2-ethoxy-1,2-dihydroquinoline (21 mg). The solution was stirred at room temperature under nitrogen for 15 h and then evaporated to dryness. The residue was dissolved in ethyl acetate, washed with 1M HCl, 5% NaHCO$_3$ and brine, dried and filtered. Evaporation of the solvent gave an oil which on chromatography over flash silica gel furnished the title compound from the dichloromethane:ethyl acetate (4:1) eluates as a white solid, crystallized from dichloromethane-petroleum ether (58 mg) m.p. 107°–108°, [α]$_D$ −7.9° (acetone).

(d) Intermediate 4

[2R-[2(R*),2(S*),2(S*)]]-2-[[2-[(5-Amino-5-carboxy-1-oxopentyl)amino]-3-mercapto-1-oxopropyl]amino-4,5-hexadienoic acid Intermediate 3 (20 mg) was dissolved in trifluoroacetic acid (1 ml, freshly distilled); anisole (0.1ml) was added and the solution was refluxed under argon for 30 mins. The mixture was cooled and trifluoroacetic acid was removed in vacuo. The residue was taken up in water, washed with ethyl acetate and freeze dried to give the title compound as a white solid (8 mg) $^1$H NMR (500 MHz, D$_2$O, $\gamma$), 5.04 (t, 7 Hz, $\gamma$--H of allene), 4.71 (m, obscured, 2H, ==), 4.43 (t, 5 Hz, $\alpha$-H), 4.37 (m, $\alpha$-H), 2.54(m, 1H, $\beta$-H of allene), 2.39-2.21 (complex 3H, $\beta$-H of allene+$\beta$-H's of cys), 1.78-1.50 (m, 4H $\gamma$H$_2$+$\beta$-H$_2$ of $\alpha$-AAA). Mass (ZAB, FAB): 745 (MH+) (disulphide).

EXAMPLE 1

Intermediate 4 (3 mg) was mixed with dithiothreitol (2 mM, 0.189 ml) ascorbic acid (1 mM, 0.189 ml) and ferrous sulphate (0.1 mM, 0.189 ml) and the pH of the solution was adjusted to 7.7-8.0 with 200 mM NaOH. Catalase (0.01 ml, Sigma standard preparation 600 units/ml) was added, followed by isopenicillin N synthetase (6 ml, 3.16 I.U. prepared from *A. chrysogenum* IMI 237183 as described in Preparation 1 above with subsequent chromatography over Sephadex G10 (Pharmacia) loaded with 50 mM NH$_4$HCO$_3$). The reaction mixture was divided equally into 3 pots and each was incubated at 27° for 1 h on a shaker (250 r.p.m.). Dithiothreitol (30 $\mu$l containing 2 mmol) was added to each pot after 15 min. At the end of 1 h the reaction was stopped by adding acetone (70% v/v) and the precipitated protein was removed by centrifugation (20,000 r.p.m. for 5 min.). Acetone in the supernatant was aspirated away under nitrogen and the remaining aqueous phase was freeze dried.

From the freeze dried material, the following compounds were isolated by electrophoresis (pH 3.5, 4 KV, 1 hr) followed by HPLC (NH$_4$HCO$_3$) buffer, reverse phase column):

(a)

6$\beta$-[(5-Amino-5-carboxy-1-oxopentyl)amino]-7-oxo-3$\beta$-propadienyl-4-thia-1-azabicyclo[3.2.0]heptane-2-carboxylic acid $^1$H (500 MHz, D$_2$O): 5.43 (d, 4 Hz, 1H, $\beta$-lactam) 5.34 (d, 4 Hz, 1H, $\beta$-lactam) 5.11 (dt, 7, 8.6 Hz, 1H, H$\beta$) 4.81 (m, obscured by HoD, 2H, H$_2$-$\gamma$) 3.60 (t, 7 Hz, 1H, $\alpha$-H of amino adipic) 2.28 (t, 7 Hz, 2H, $\delta$-H's of amino adipic) 1.84-1.70 (m, 2H, $\delta$-H's of amino adipic) 1.67-1.52 (m, 2H, $\delta$-H's of amino adipic) $^1$H NMR (500 MHz, CD$_3$CN/D$_2$O/HCOOH): 4.87 (1H, d, J 7 Hz) IR: 1956 (allene), 1765 ($\beta$-lactam)cm$^{-1}$ Mass (FAB, EX MeOH/GLY/OX): 370 (MH+, 70%) 420 (M+-MeOH, 24%) HPLC: Retention time 13 min (Buffer 50 mmolar NH$_4$HCO$_3$ Reverse phase column, 1200 psi pressure) electrophoresis: Mobility 14 cm under 4 KV for 1 hr.

(b)

6$\beta$-[(5-Amino-5-carboxy-1-oxopentyl)amino]-7-oxo-3$\alpha$-propadienyl-4-thia-1-azabicyclo[3.2.0]heptane-2-carboxylic acid $^1$H NMR (500 MHz, D$_2$O) 5.33 (d, 3.5 Hz, 1H, $\beta$-lactam) 5.32 (d, 3.5 Hz, 1H, $\beta$-lactam) 5.27 (q, 7 Hz, 1H, H-$\alpha$)4.87 (m, 2H, H$_2$-$\gamma$) 3.60 (t, 1H, 7 Hz, $\alpha$-H of amino adipic) 2.30 (t, 2H, 7 Hz, $\delta$-M's of amino adipic) 1.84-1.70 (m, 2H, $\beta$-H's of amino adipic) NMR (500 MHz, CD$_3$CN/D$_2$O) 4.52 (d, 2.7 Hz, 1H, 3-H) 4.68 (m, 1H, 2-H) Mass: (FAB, EX GLY/MeOH/OX): 370 (MH+, 60), 402 (MH+ +MeOH, 8) IR: 1766 ($\beta$-lactam) 1599 (amide and COOH) cm$^{-1}$ HPLC: Retention time 14.5 min Electrophoresis: Mobility 14 cm (4 KV 1 hr).

We claim:

1. A compound of the formula

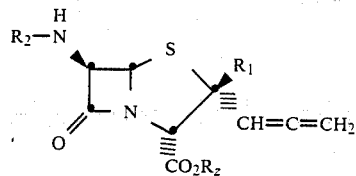

or

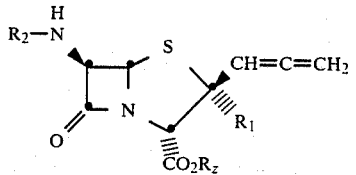

or a mixture of the two, wherein:

R$_1$ is hydrogen or a methyl group; R$_2$ is hydrogen, an amino-protecting group or a C$_1$ to C$_{20}$ acyl group; and R$_z$ is a carboxy-protecting group or hydrogen; or a salt thereof.

2. A compound of claim 1, wherein R$_2$ is (a) hydrogen;

(b) an amino-protecting group;

(c) a group of the formula

wherein R$_6$ is (i) 1,4-cyclohexadienyl, 1-cyclohexenyl, phenyl or substituted phenyl, wherein the substituents are 1 or 2 halogen, hydroxy, protected hydroxy, amino, protected amino, nitro, cyano, trifluoromethyl, C$_1$ to C$_4$ alkyl, C$_1$ to C$_4$ alkoxy, carboxy, protected carboxy carboxymethyl, protected carboxymethyl, hydroxymethyl, protected hydroxymethyl, aminomethyl, protected aminomethyl, or N-((C$_1$ to C$_4$ alkyl)sulfonyl-amino) groups;

(ii) a group of the formula

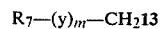

wherein y is O or S, m is 0 or 1, R$_7$ is R$_6$ as defined above, and when m is 0, R$_7$ is also 2-thienyl, 3-thienyl, 2-furyl, 3-furyl, 1-tetrazolyl, 5-tetrazolyl, 2-thiazolyl, 2-aminothiazol-4-yl, or 2-(protected amino)thiazol-4-yl;

(iii) a group of the formula

wherein R$_8$ is R$_7$ as defined above, a 2- or 3-indolyl group, a substituted 2- or 3-indolyl group of the formula

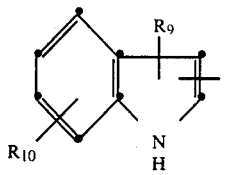

in which $R_9$ and $R_{10}$ independently are hydrogen, halo, hydroxy, protected hydroxy, $C_1$ to $C_4$ alkyl, $C_1$ to $C_4$ alkoxy, nitro, amino, protected amino, N-(($C_1$ to $C_4$ alkanoyl)amino), N-(($C_1$ to $C_4$ alkyl)sulfonylamino), or when $R_9$ and $R_{10}$ are on adjacent carbon atoms, they may be taken together to form a methylenedioxy group; a 2- or 3-benzothienyl group, a 2- or 3-substituted benzothienyl group of the formula

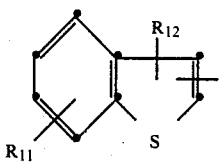

in which $R_{11}$ and $R_{12}$ are independently hydrogen, halo, hydroxy, protected hydroxy, $C_1$ to $C_4$ alkyl, $C_1$ to $C_4$ alkoxy, nitro, amino, protected amino, N-(($C_1$ to $C_4$ alkanoyl)amino), N-(($C_1$ to $C_4$ alkyl)sulfonylamino), or when $R_{11}$ and $R_{12}$ are on adjacent carbon atoms, they can be taken together to form a methylenedioxy group; a 1- or 2-naphthyl group, a substituted 1- or 2-naphthyl group of the formula

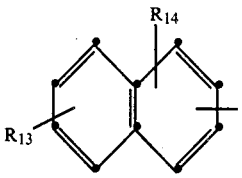

wherein $R_{13}$ and $R_{14}$ are independently hydrogen, halo, hydroxy, protected hydroxy, $C_1$ to $C_4$ alkyl, $C_1$ to $C_4$ alkoxy, nitro, amino, protected amino, N-(($C_1$ to $C_4$ alkanoyl)amino), N-(($C_1$ to $C_4$ alkyl)sulfonylamino), or when $R_{13}$ and $R_{14}$ are on adjacent carbon atoms, they can be taken together to form a methylenedioxy group; and W is amino, protected amino, carboxy, protected carboxy, or sulfonato;

(iv) a group of the formula

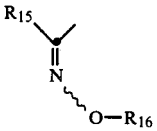

wherein $R_{15}$ is phenyl, p-(O-(homoserine))phenyl thien-2-yl, fur-2-yl, 2-aminothiazol-4-yl, 2-(protected amino)thiazol-4-yl, 5-amino-1,2,4-thiadiazol-3-yl, 5-(protected amino)-1,2,4-thiadiazol-3-yl, 4-aminopyridin-2-yl, 4-(protected amino)pyridin-2-yl, 2-aminopyridin-6-yl, 2-(protected amino)pyridin-6-yl, 2-aminopyrimidin-4-yl, 2-(protected amino)pyrimidin-4-yl, 4-aminopyrimidin-2-yl, or 4-(protected amino)pyrimidin-2-yl; and $R_{16}$ is hydrogen, methyl, ethyl, propyl, 2-carboxyisopropyl, 2-(protected carboxy)isopropyl, carboxymethyl, (protected carboxy)methyl, cyclopropyl, cyclobutyl, cyclopentyl, benzyl, phenyl, 4-fluorophenyl, 4-chlorophenyl, 3-(trifluoromethyl)phenyl, 3-(ethoxycarbonyl)phenyl, 2-methylphenyl, 4-methylphenyl, 3,4-dichlorophenyl, or 2,4-dichlorophenyl; or (v) a group of the formula

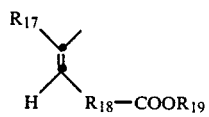

wherein $R_{17}$ is phenyl, furyl, thienyl, oxazolyl, isoxazolyl, aminoisoxazolyl, (protected amino)isoxazolyl, thiazolyl, aminothiazolyl, or (protected amino)thiazolyl; $R_{18}$ is $C_1$ to $C_3$ alkyl; and $R_{19}$ is hydrogen or a carboxy-protecting group;

(vi) a group of the formula

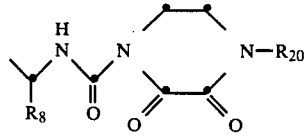

wherein $R_8$ is as defined above and $R_{20}$ is $C_1$ to $C_6$ alkyl or $C_1$ to $C_6$ substituted alkyl;

(vii) a group of the formula

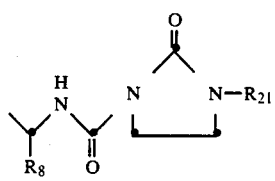

wherein $R_8$ is as defined above and $R_{21}$ is hydrogen, $C_1$ to $C_4$ alkylsulfonyl, a group of the formula $$-N=CH-R_8$$

(wherein $R_8$ is as defined above); a group of the formula $$-COR_{22}$$

wherein $R_{22}$ is hydrogen, $R_8$, $C_1$ to $C_6$ alkyl or $C_1$ to $C_6$ substituted alkyl; or (viii) a group of the formula

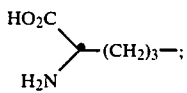 (L)

-continued

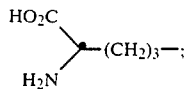

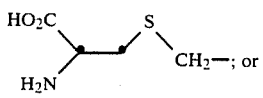

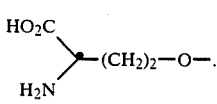

3. A compound of claim 2, wherein $R_1$ and $R_z$ are hydrogen.

4. A compound of claim 3 wherein $R_2$ is a group of the formula

wherein $R_6$ is a group of the formula

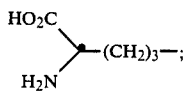

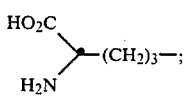

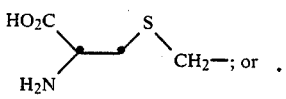

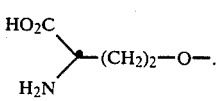

5. A compound of claim 4, wherein $R_6$ is a group of the formula

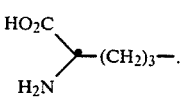

6. A compound of the formula

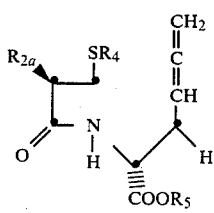

wherein $R_{2a}$ is a group of the formula:

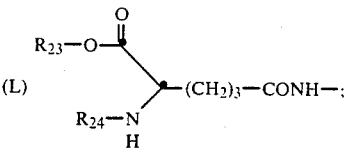

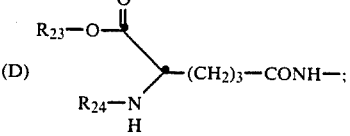

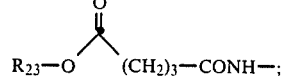

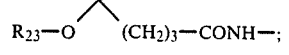

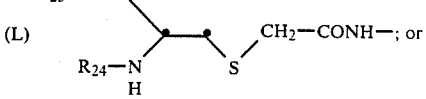

and wherein:
$R_4$ is hydrogen or p-methoxybenzyl;
$R_5$ is carboxy-protecting group or hydrogen;
$R_{23}$ is a carboxy-protecting group or hydrogen; and
$R_{24}$ is hydrogen or an amino-protecting group; or a salt thereof.

7. A compound of claim 6, wherein:
$R_{2a}$ is a group of the formula

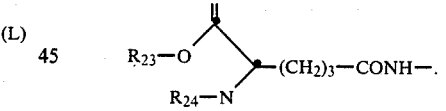

8. A compound of claim 7, wherein:
$R_{23}$ is p-methoxybenzyl;
$R_{24}$ is p-methoxybenzyloxycarbonyl; and
$R_5$ is diphenylmethyl.

9. A compound of claim 7, wherein $R_{23}$, $R_{24}$, and $R_5$ are each hydrogen; or a salt thereof.

10. A compound of the formula

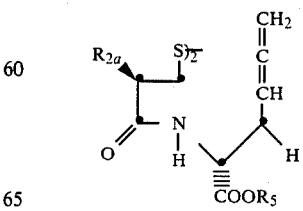

wherein: $R_5$ is hydrogen or a carboxy-protecting group and $R_{2a}$ is a group of the formula

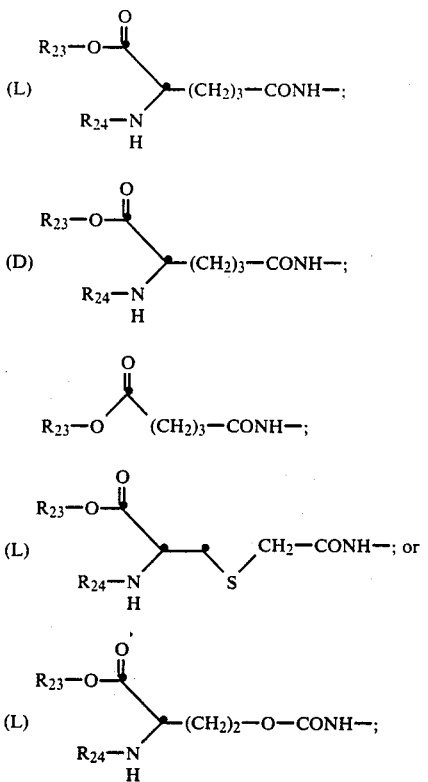

wherein
R₂₃ is a hydrogen or a carboxy-protecting group;
R₂₄ is hydrogen or an amino-protecting group; or a slat thereof.

11. A process for making a compound of claim 1, wherein $R_2$ is a group of the formula

wherein $R_6$ is a group of the formula

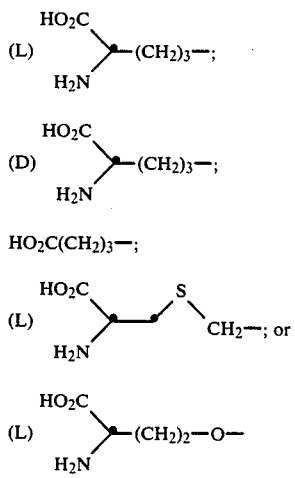

and $R_z$ is hydrogen; or a salt thereof; which comprises combining a substrate compound of the formula

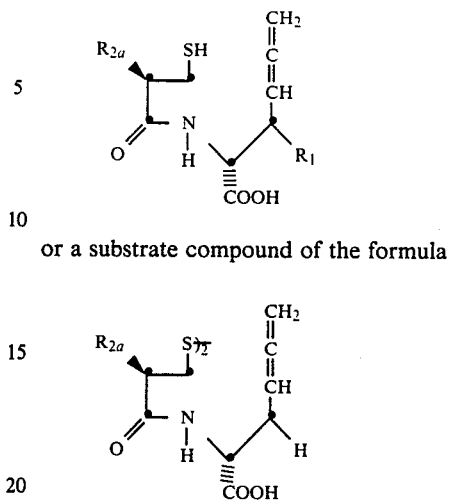

or a substrate compound of the formula

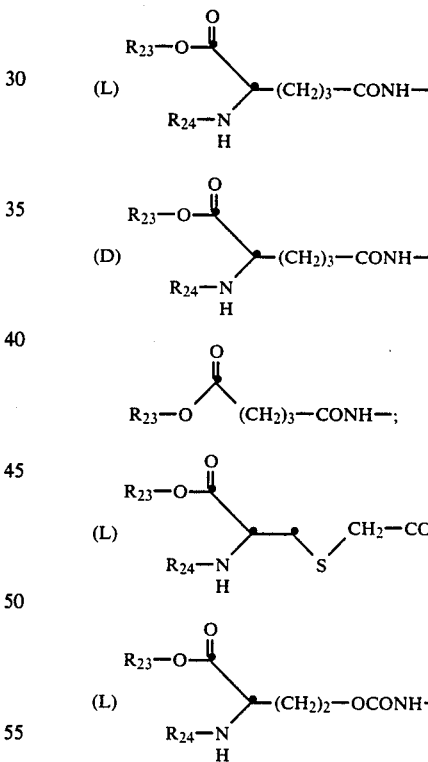

with the enzyme known as isopenicillin N synthetase, wherein in the above formulas
$R_1$ is hydrogen or methyl; and
$R_{2a}$ is a group of the formula:

wherein $R_{23}$ and $R_{24}$ are hydrogen.

12. A process of claim 11, which comprises combining the substrate compound and the isopenicillin N synthetase enzyme in a buffer solution and incubating the solution between about 0° C. to about 40° C. at a pH of between about 6 to aobut 9.

13. A process of claim 12, which comprises combining the substrate compound and the isopencillin N synthetase enzyme in a buffer solution and incubating the solution between about 20° to 30° C. at a pH of between about 7 to 8.

14. A process of claim 13, which comprises combining a substrate compound of the formula

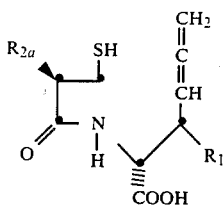

with the enzyme known as isopencicillin N synthetase.

15. A process of claim 14, wherein:

$R_1$ is hydrogen;

$R_{2a}$ is a group of the formula

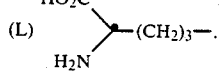(CH₂)₃—CONH—; and $R_6$ is a group of the formula

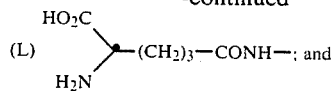

16. A process of claim 15, wherein the substrate compound and the isopenicillin N synthetase are incubated in a buffer solution containing dithiothreitol at a concentration of from about 1 to about 5 millimolar, ferrous ions at a concentration from about 0.1 to about 1 millimolar, ascorbate ions at a concentration from about 1 to about 5 millimolar, and catalase at a concentration of about 1000 to about 5000 Sigma units per milliliter.

* * * * *